United States Patent [19]

Munkholm

[11] Patent Number: 5,506,148
[45] Date of Patent: Apr. 9, 1996

[54] METHOD FOR ACTIVATION OF POLYANIONIC FLUORESCENT DYES IN LOW DIELECTRIC MEDIA WITH QUATERNARY ONIUM COMPOUNDS

[75] Inventor: Christiane Munkholm, Salem, Mass.

[73] Assignee: Ciba Corning Diagnostics Corp., Medfield, Mass.

[21] Appl. No.: 214,340

[22] Filed: Mar. 16, 1994

Related U.S. Application Data

[62] Division of Ser. No. 116,436, Sep. 3, 1993.

[51] Int. Cl.$^6$ .................................................. G01N 33/00
[52] U.S. Cl. .................... 436/111; 436/113; 436/133; 436/136; 436/163; 436/172; 422/82.07; 422/82.08; 356/39; 356/412; 204/291
[58] Field of Search ............................ 436/111, 103, 436/172, 163, 133, 127, 62, 113, 136; 422/82.07, 82.08; 356/39, 412; 204/290 F, 291, DIG. 9

[56] References Cited

U.S. PATENT DOCUMENTS

| | | | |
|---|---|---|---|
| Re. 31,879 | 5/1985 | Lubbers et al. | 436/133 |
| Re. 33,064 | 9/1989 | Carter et al. | 436/34 |
| 4,882,288 | 11/1989 | North et al. | 436/525 |
| 5,005,572 | 4/1991 | Raemer et al. | 128/207.14 |
| 5,005,752 | 4/1991 | Raemer et al. | 128/207.14 |
| 5,096,671 | 3/1992 | Kane et al. | 422/82.07 |
| 5,119,463 | 6/1992 | Vurek et al. | 385/129 |
| 5,156,976 | 10/1992 | Slovacek et al. | 436/164 |
| 5,273,716 | 12/1993 | Northrup et al. | 422/82.07 |
| 5,277,872 | 1/1994 | Bunkert et al. | 422/82.07 |
| 5,294,402 | 3/1994 | Schrepp et al. | 422/57 |

FOREIGN PATENT DOCUMENTS

91/05252 4/1991 WIPO.

OTHER PUBLICATIONS

Diaz Garcia, M. E., et al, Talanta 33(3), 255–264 (1986).
Harlow, G. A., et al, Anal. Chem., 28, 787–791 (1956).
Huston, M. E., et al, J. Amer. Chem. Soc., 111, 8735–8737 (1989).
Kobos, R. K., et al, Anal. Chem., 54, 1976–1980 (1982).
Lakowicz, J., "Principles of Fluorescence Spectroscopy", 1986 Plenum Press, New York, pp. 190, 187–208.
Lopez, M. E., et al, Anal. Chem., 54, 2085–2089 (1982).
Mills, A., et al, Anal. Chem., 64, 1383–1389 (1992).
Mills, A., et al, Proceedings SPIE Optical Conference: Jan. 1993.
Motomizu, S., et al, Analytica Chimica Acta, 120, 267–277 (1980).
Mulder, W. J., et al, J. Org. Chem., 53, 3353–3355 (1988).
Munkholm, C., et al, Anal. Chem., 58, 1417–1430 (1986).
Munkholm, C., et al, J. Amer. Chem. Soc., 112, 2608–2612 (1990).
Munkholm, C., et al, Talanta 35, 109–112 (1988).
Orellana, G., et al, Anal. Chem., 64, 2210–2215 (1992).
Seitz, W. R., et al, CRC Critical Reviews in Anal. Chem., 19, 135–173 (1988).
Severinghaus, J. W., et al, J. Applied Physiology, 13, 515–520 (1958).
Starks, C. M., et al, "Phase Transfer Catalysis, Priciples and Techniques", 1978 Academic Press, New York, pp. 1–21.
Szmacinski, H., et al, Anal. Chem., 65, 1668–1674 (1993).
Wehry, E. L., "Modern Fluorescence Spectroscopy", 1976 Plenum Press, New York, pp. 93–101.
Wolfbeis, O. S., et al, Anal. Chem., 60, 2028–2030 (1988).
Wolfbeis, O. S., et al, Analytica Chimica Acta, 185, 321–327 (1986).
Wolfbeis, O. S., et al, Mikrochimica Acta, I, 153–158 (1984).
Mills, et al, Analyst, 118, 839–843 (1993).
Mills, et al, Analytica Chimica Acta, 285, 113–123 (1994).

*Primary Examiner*—Robert J. Warden
*Assistant Examiner*—N. Bhat
*Attorney, Agent, or Firm*—Arthur S. Morgenstern; Nicholas I. Slepchuk, Jr.; Judith A. Roesler

[57] ABSTRACT

The invention pertains to a method for generating the fluorescence of polyanionic fluorophores in low dielectric media with fluorescence activation produced by specific quaternary onium compounds. The method may be used for measuring an analyte and may be useful in sensor devices.

14 Claims, 8 Drawing Sheets

HPTS

FIG. 5A

FLUORESCEIN

FIG. 5B

CASCADE BLUE,
ETHYLENEDIAMINE,
TRISODIUM SALT

FIG. 5C

SNAFL

METHOD FOR ACTIVATION OF POLYANIONIC FLUORESCENT DYES IN LOW DIELECTRIC MEDIA WITH QUATERNARY ONIUM COMPOUNDS

This is a divisional of copending application(s) Ser. No. 08/116,436 filed on Sep. 3, 1993, now allowed U.S. patent pending.

BACKGROUND OF THE INVENTION

A. Field of the Invention

The present invention pertains to a method of generating the fluorescence of polyanionic fluorophores in low dielectric media with fluorescence activation produced by specific quaternary onium compounds. The chemistry may be used in solution phase or in a solid phase such as a low dielectric polymer coating, and when used as a coating can function as a fluorescent optical sensor material for analytes which are permeable to the coating and capable of modulating the fluorescence in a specific manner.

B. Description of Related Art

When the spectral properties of a colorimetric or fluorimetric dye are modulated by a specific analyte, in a concentration dependent manner, the dye is said to be capable of functioning as a transducer for said analyte. A large body of technology using colorimetric and fluorimetric dyes as transducers now exists. Historically these dyes have been used in solution analyses, but they are finding renewed applications as immobilized indicators on optical surfaces such as optical fibers, (W. Rudolf Seitz, CRC Critical Reviews in Anal. Chem., 1988, 19, 135).

Fluorescence based optical detection systems are preferred over those based on colorimetric or absorbance based detection schemes because fluorescence is more sensitive by several orders of magnitude since it is a zero background phenomenon. Also, more spectral discrimination may be incorporated into the analysis as one employs excitation and emission wavelengths as selectivity parameters. Additional selectivity is possible by measuring fluorescence phenomena other than direct intensity, such as fluorescence lifetimes and polarization. A technological advantage of fluorescence analysis is the compatibility of fluorescence with laser excitation.

The photophysical properties of fluorophores are intimately related to their molecular structure as well as to the nature and charge of any substituents on the central structure. Many of the fluorophores commonly used for optical sensors are negatively charged and are typically used in polar media.

The immobilization of fluorophores as transducers for optical sensors has been accomplished with a variety of methods, generally falling into four classes: 1)adsorption to a charged surface or charged polymer (Oreliana, G., Moreno-Bondi, M. C., Segovia, E., Marazuela, M. C., Analytical Chemistsry, 64, 2210–2215, 1992), 2) entrapment in a reservoir or polymer with a cover membrane (Wolfbeis, O. S., Weis, L. J., Leiner, M. J. P., Ziegler, W. E.., Analytical Chemistry, 60, 2028–2030, 1988), 3) covalent attachment as a monolayer to the substrate surface (Wolfbeis, O. S., Offenbacher, H., Kroneis, H., Marsoner, H., Mikrochimica Acta, I, 153–158, 1984) and 4) covalent attachment as a copolymer grafted to the surface (Munkholm, C., Walt, D. R., Milanorich, F. P., Klainer, S. M., Anal. Chem. 58, 1427–1430, 1986).

All of these methods have inherent limitations which may be a problem for particular applications. Anionic dyes that are immobilized by adsorption to a charged surface may have poor stability in aqueous samples and the dye will not be protected from other ionic constituents in the sample. Immobilization via entrapment in a liquid or gel reservoir phase requires the addition of a barrier membrane which serves to contain the dye while being permeable to the analyte of interest. For clinical applications this second membrane is typically a hydrophobic polymer. However, dual-phase optical sensors, prepared with two layers of incompatible material, often suffer from malfunction due to pinhole leaks and also exhibit decreased response times due to diffusional requirements through the hydrophobic membrane. Optical sensors with single layer coatings have been prepared with covalently immobilized dyes and dye-copolymers. However a covalent immobilization can be difficult to achieve while preserving the dye's intrinsic photophysical properties. Even with covalent immobilization of the transducer a barrier membrane will be necessary if the sensor requires that the dye be isolated in a particular internal electrolyte or buffer system.

If one could use a fluorophore in a hydrophobic or nonpolar polymer membrane the optical sensor components could be chemically partitioned from the aqueous sample. However, polyanionic dyes are extremely sensitive to the microenvironmental polarity of the solvent or solid matrix surrounding the fluorophore and many in this class are not fuorescent in nonpolar media. Fluorescein, which has a very high, pH dependent quantum yield in aqueous samples, has a nearly totally quenched fluorescence when observed in the nonpolar environment of a low dielectric solvent such as hexane or benzene, or when included in a hydropohobic polymer such as polystyrene. In such an environmentally quenched state the dye is not useful as an analytical reagent.

SUMMARY OF INVENTION

The present invention describes a method that reverses the fluorescence quenching effect of low dielectric media on polyanionic dyes by inclusion of quaternary ammonium compounds to a formulation used for coating substrates for the preparation of optical sensor surfaces. The quenching phenomenon can be reversed and the resulting activated fluorescence can be utilized for analytical purposes by coupling the specific chemical phenomena known to affect the photophysical properties, such as acid-base equilibria or quenching effects, to an analyte that is capable of penetrating the low dielectric media and interacting with the activated fluorophore. One can monitor any fluorescence parameter such as absolute intensity, phase-modulation, polarization, lifetimes, or phosphorescence for the spectral analysis.

Although the instant invention deals primarily with ammonium compounds, it will be understood by those with skill in the art that ammonium compounds are merely one example of a class of compounds called onium compounds. Other members of the onium class include, for example, phosphonium compounds such as tetrabutylphosphonium bromide, which have as a common characteristic an alkyl or aryl derivatized cationic function combined with an anionic counterion. It is expected that other onium compounds perform similarly to the ammonium compounds, particularly if one chooses the proper counterion and alkyl ligand. Throughout this discussion, the novel performance will be discussed relative to the entire class of onium compounds.

In accordance with the invention the fluorescent dye must be a polyanionic dye which undergoes a complete loss of fluorescence when solubilized in low dielectric media such as hexane or toluene, or solid media such as polystyrene. Dyes of this class include but are not limited to fluorescein and derivatives, sulfphonated pyrenes and derivatives, seminaphthorhodafluors and derivatives, and seminaphthofluoresceins and derivatives.

The addition of a compound which is capable of being solubilized in the nonpolar environment and which has a positive charge, such as a quaternary ammonium compound, will form an ion complex or aggregated complex with the polyanionic dye dissolved in the media. The activating onium compounds (AcOC) exemplified in this invention are alkyl and aryl substituted ammonium compounds, such as tetrabutylammonium hydroxide, and an acrylate copolymer containing an ammonium functional group. Both of these activators have an organic ligand soluble in a low dielectric media and a cationic ammonium moiety which forms the charge-charge interaction with the polyanionic dye. The association and assembly of these two charged species results in aggregated microdomains, and in this more polar microenvironment the dye molecule is shielded from the quenching effect of the low dielectric bulk media. Using this method, dyes that have a very high quantum yield in water, such as fluorescein and hydroxypyrenetrisulphonic acid (HPTS), will be restored to the same or similar levels of relative photon emission when used in solvents that typically quench the fluorescence. Other AcOC compounds having similar properties can also be used.

In one embodiment, the fluorescence activation is demonstrated in solution, with the addition of the AcOC to polyanionic fluorophores in low dielectric solvents. The fluorescence signal is enhanced by 50–2000 fold, and occurs with both pH sensitive and non-pH sensitive polyanionic dyes.

In a second embodiment the fluorescence activation is demonstrated in the solid phase in low dielectric polymers on glass substrates. A fluorophore/polymer solution used for a membrane coating is activated with an AcOC, and remains capable of being fluorescent in the coating polymer after evaporation of the coating solvent. The dye continues to function in the coating with its chemically specific properties. For example, a $CO_2$ sensor based on pH equilibria has been prepared as well as an $O_2$ sensor based on fluorescence quenching. Importantly, these hydrophobic membranes are stable in liquid samples, allowing the preparation of very thin fluorescent films for optical sensor fabrication.

A third embodiment utilizes a polymer that contains an ammonium functional group which serves for both flourescence activation and membrane formation, demonstrating that it is possible to combine the fluorescence activation mechanism with the polymer support.

The disclosed invention of fluorescence activation enables the use of some of the most familiar and highly utilized fluorophores in environments where they were previously inoperative due to quenching effects of the media. The activated fluorophores also retain their characteristic chemical properties, i.e. pH sensitivity. With this invention one may prepare sensor coatings where the transducer is rendered functional by the addition of the activating compound. Furthermore, the sensor membrane is partitioned from the clinical sample due to insolubility of the nonpolar membrane with the aqueous sample, thus minimizing the need for cover membranes or covalent chemistry as a method of preventing wash out of the dye. One can then prepare sensors for any analyte capable of permeating the membrane containing the activated fluorophore.

As the low dielectric sensor coatings are prepared with hydrophobic polymers, polar analytes such as electrolytes may be prevented from entering the sensor media unless complexed with a vector molecule. Analytes that are capable of diffusing through the coating and into the sensor microdomains created by the activated complex are ones that permeate through a low dielectric medium, such as vapor or gaseous analytes. Nonpolar analytes could diffuse directly into the sensor from the liquid phase as well. Examples of analytes that could be coupled to this chemistry would be $O_2$, $CO_2$, and $NH_3$, which can be detected by various fluorescent transducers. Also, any reaction that produces a gas, such as an enzyme system that yields ammonia, or a chemical catalysis system that has a low dielectric byproduct, could be coupled to the sensor layer containing the appropriate fluorescent transducer.

The method described herein is to be distinguished from the colorimetric readout system described in U.S. Pat. No. 5,005,572 (Raemer, Walt, Munkholm). This prior art describes the first observation of a useful interaction occurring between pH sensitive colorimetric dyes and quaternary onium compounds (referred to as phase transfer enhancers or catalysts), for the purpose of providing a visual colorchanging readout system in a medical device. The addition of the phase transfer catalyst did not produce the appearance of color but rather sensitized the rate of acid/base response of the dye as a solid phase transducer for respiratory $CO_2$ in an endotracheal tube. The colorimetric dyes used in U.S. Pat. No. 5,005,572 were at a concentration that could be observed with the naked eye and there was no issue related to activating or increasing the detectability of the transducer for either visual or instrumental purposes. Raemer et al. claimed the use of all phase transfer catalysts, and the invention disclosed herein is confined to the specific quaternary ammonium compounds that enhance fluorescence. Also, no distinction was made in Raemerover the polarity of the substrate used to support the transducer. The dyes were all prepared in aqueous media and were never deposited from or used in a low dielectric solvent. In contrast, the present invention is directed to the activation of fluorescent dyes in nonpolar, quenching environments, and the subsequent ability of the activated fluorophores to act as transducers in hydrophobic membranes. Furthermore, the instant invention is not limited to the pH sensitive fluorophores discussed in U.S. Pat. No. 5,005,572, and the activator is not limited to the phase transfer catalysts discussed in Raemer. Another patent application, WO 91/05252 (Mills, McMurray), duplicates the disclosure of U.S. Pat No. 5,005,572 for the colorimetric readout of respiratory $CO_2$ in an intubation device. The work disclosed herein describes three novel improvements over the prior art: 1) a generic method for the fluorescence activation of polyanionic fluorophores in nonpolar (i.e., low deielectric) media, 2) the preparation of hydrophobic fluorescent membranes prepared from low dielectric polymers, and 3) the subsequent use of the polymer coatings as optical sensors in instrumentation utilizing any of the fluorescent modes of signal transmission.

The method of this invention is useful for either in vitro or in vivo applications, including blood gas instruments and optical fibers or planar waveguides used as components of sensors, both in medical or environmental sensing formats. Although we describe measurements of direct fluorescence intensity, we are not limiting the invention to intensity measurements. Any mode of fluorescence, such as lifetime measurements, phase-modulation (Szmacinski, H., Lakowicz, J. R., Analytical Chemistry, 65, 1668–1674, 1993), or polarization, may be coupled to the analyses as well as the use of detection schemes employing multiple fluorophores, such as energy transfer based systems. Non fluorescent polyanionic dyes may also be used in these energy transfer systems, as well as being used in analytical applications where only colorimetric dyes are used.

DETAILED DESCRIPTION OF THE INVENTION

A. Background theory

The sensitivity of fluorophores to the polarity of their surroundings is a well characterized property of fluorescence and one often exploited for analysis of microenvironmental phenomena. The Lippert equation, relating the influence of the solvent on the ground state and the excited state dipoles is used to predict the difference between the energies of the excitation and emission bands, known as the Stokes shift, expected for a given fluorophore in media of varying polarity (Lakowicz, J., Principles of Fluorescence Spectroscopy, Plenum Press, New York, p. 190). Both the dielectric and the refractive index of the solvent contribute to a reactive field induced in the solvent surrounding the dye, and the interaction of the dipole of the dye with this field determines the solvent relaxation state and the energy of the emission wavelength.

The quantum yield of a dye will be affected by solvent polarity also, as well as by numerous other factors. Apart from the general solvent effects described by the Lippert equation, solvents can also have specific chemical effects, such as hydrogen bonding, on a fluorophore. How the quantum yield of a particular dye will be affected by a solvent will depend on the relative importance of both general and specific solvent effects. Also, chemical effects due to extraneous compounds can alter the quantum yield.

When evaluating a dye for sensitivity to solvent polarity, it is known that fluorophores which have the largest changes in dipole moment between the ground state and the excited state will be the most sensitive to solvent polarity (J. R. Lakowicz, Principles of Fluorescence Spectroscopy, 1986 Plenum Press New York, 3rd Edition, pp 187–208). The fluorescence quantum yield and energy are affected by the ability of solvent molecules to respond to the dipole changes occurring upon excitation of the dye, a phenomenon known as solvent relaxation. Although solvent polarity or dipole is an important factor in determining this solvent stabilization of the excited state, other factors that affect this phenomenon include solvent structure, dye structure, microviscosity, and temperature. (E. L. Wehry, Modern Fluorescence Spectroscopy, 1976 Plenum Press, New York, pp 93–101)

Nonpolar solvents, such as hexane, have little or no dipole moment. Consequently, the solvent relaxation due to dipole reorientation is unimportant, and fluorophores dissolved in nonpolar solvents exhibit a small Stokes shift compared to that observed in polar solvents. The quantum yield as a function of dipole is less predictable; some fluorophores, such as anilinonaphthalene sulfonic acid (ANS), have a higher quantum yield in nonpolar solvents than in polar media. Other fluorophores, such as fluorescein, exhibit their high quantum yield state in polar aqueous solvents, and are quenched in nonpolar solvents.

The quantum yield of a dye in a given solvent can undergo enhancement or activation of fluorescence due to specific chemical effects that alter either the structure of the dye or the microenvironment of the dye. Examples that alter the structure of the dye are the activation of the fluorescence of fluoresceinamine by reaction with acyl halides (Munkholm, C., Parkinson, D-R., Walt, D. R. , Journal of the American Chemical Society, 112, 2608–2612, 1990) and the fluorescence activation by chelation with an electron withdrawing group (Huston, M. E., Akkaya, E. U., Czarnik, A. W., Journal of the American Chemical Society, 111, 8735, 1989). An example of a specific chemical effect that alters the environment of the dye is the use of surfactants which have been observed to affect the absorptivity, Stokes shift, and/or quantum yield of some dyes(Diaz Garcia, M. E., Sanz-Medel, A., Talanta, 33(3), 255–264, 1986). Surfactants are amphiphilic molecules containing a distinct hydrophobic region of carbon chains (8–18 atoms, unbranched) and hydrophilic, ionic head groups. In water, the lengthy alkyl chain of the surfactant assembles via hydrophobic interactions into an organized assembly known as a micelle. Dyes that become solubilized in the less polar pseudo-phase of the micelle will experience a different environment, and if the dye's photophysical properties are polarity dependent one observes an alteration in the extinction coefficient, Stokes shift, and/or quantum yield. This technique has been exploited to sensitize solution-based analyses, as well as used for determination of the critical micelle concentration (cmc) for a given surfactant. When surfactants are added to a nonpolar solvent, such as benzene or carbontetrachoride, the polar headgroups aggregate, forming reverse micelies.

Phase transfer catalysts (PTC) are another class of amphiphilic molecules as they are quaternary ammonium ions and are similar to surfactants as they have an organic moiety associated with a charged head group and a counterion. The polar group can have varied constituents and charges, and the non-polar region can be substituted with alkyl or aryl groups of varying length and nature. It is the length of the alkyl group that forms the distinction between phase transfer catalysts and surfactants, with the length being typically 8– 18 carbon atoms for the surfactant class and less than 8 carbons for the PTC class. Many of the AcOCs used in this work are classified as phase transfer catalysts although the hexadecyltrimethylammonium hydroxide has an alkyl chain that exceeds the typical length for a PTC.

Given the polar and nonpolar regions of a PTC molecule they have been almost exclusively exploited for their ability to facilitate syntheses occurring at the boundaries of hydrophobic and hydrophilic phases of an inhomogenous solution of reagents. (Starks, C. M., Liotta, C., Phase Transfer Catalysis, Principles and Techniques, 1978, Academic Press, New York, pp 1–21) Because of the short length of their alkyl groups PTCs are reported to not form micelles (Mulder, W. J., Engberts, J. B. F. N., Journal of Organic Chemistry, 53, 3353–3355, 1988). Quaternary ammonium ions have been used for ion-pair extraction with triphenylmethane dyes (Motomizu, S., Toei, K., Analytica Chimica Acta, 120, 267–277, 1980) but they have never been reported to activate the photophysical properties of fluorescent or colorimetric dyes.

B. Principle of fluorescence enhancement in low dielectric media with specific onium compounds The method of this invention is based on a novel fluorescence activation chemistry produced by addition of specific onium compounds, such as tetrabutylammonium hydroxide (TBAH), to a low dielectric media wherein a polyanionic fluorophore is quenched of fluorescence. Typically the fluorophore is one that has a high quantum yield in aqueous or polar media and is rendered nonfluorescent in nonpolar media, such as hexane. The addition of the activation reagent causes the dye to display when in a nonpolar liquid or solid media, the photophysical properties typically observed in aqueous media.

Figure 1:
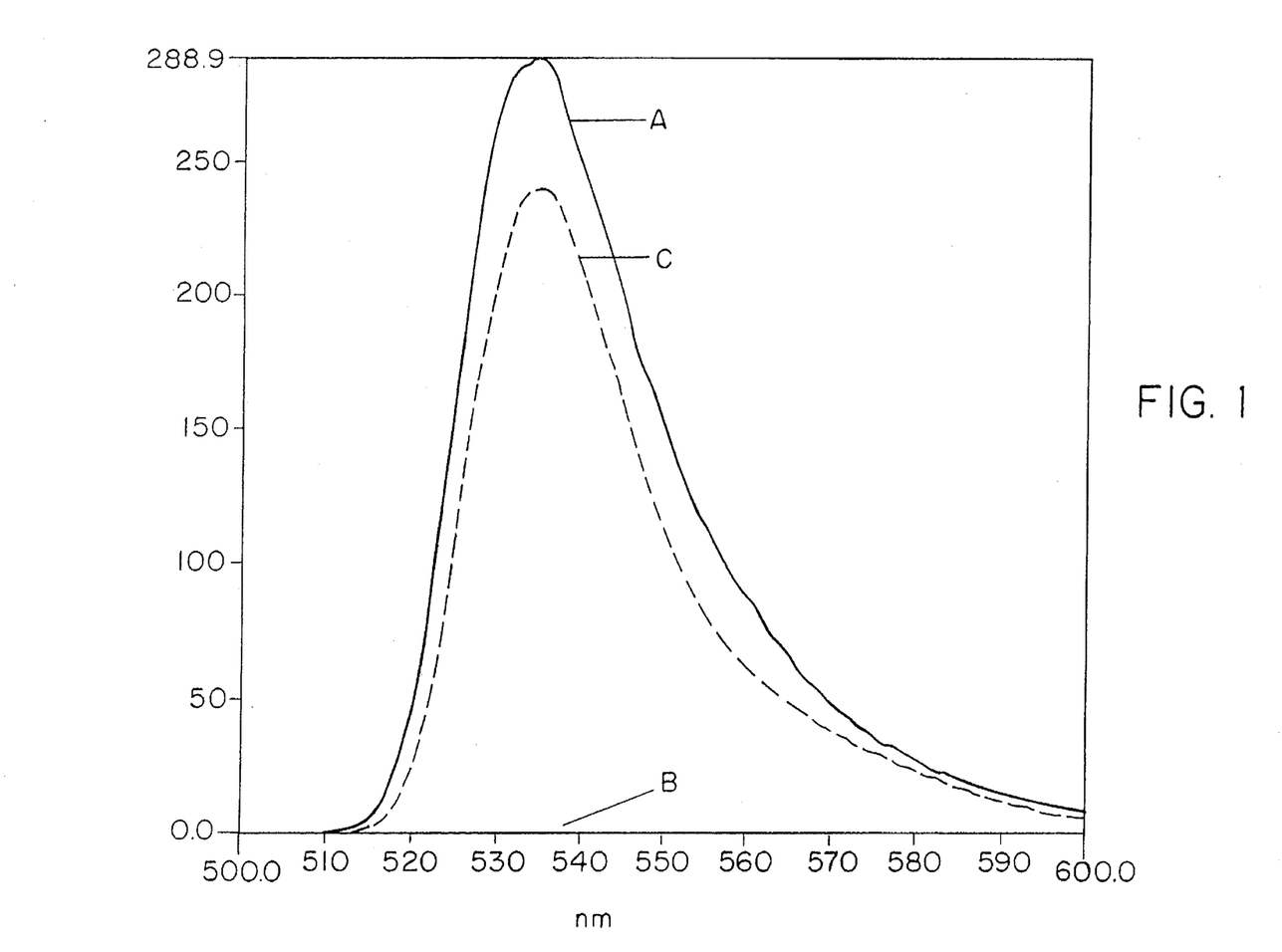
FIG. 1 shows comparative flouorescence emission of fluorescein in water, toluene, and toluene plus AcOC.

FIG. 1 shows the comparative emission spectra of identical concentrations ($5 \times 10^{-7}$ M) of fluorescein in: a) aqueous buffer, pH 7.5, b) toluene, and c) toluene with $5 \times 10^{-4}$ M tetrabutylammonium hydroxide included. The solutions were all excited with a 488 nm source (Perkin Elmer, LS-50, Fluorimeter), and emission collected with a 530 nm filter inserted. The fluorescence in the buffer is typical of fluorescein in a basic aqueous state where the quantum yield is in the range of 0.90. The same concentration of fluorescein in toluene shows zero fluorescence emission; after addition of the tetrabutylammonium hydroxide the fluorescence is restored to 83% of the signal observed in the aqueous sample. The dye is fully activated when the AcOC/dye molar ratio is approx. 1000. This molar ratio of AcOC/dye for complete activation is a function of the particular dye and dye concentration, the particular AcOC, and the solvent employed in the titration.

Given the amphiphilic nature of both the dye and the activating compounds it is probable that self-assembly via their charge-charge interactions occurs, and these aggregates acquire a much more polar microenvironment than that of the bulk media. When the dye becomes solubilized in this polar domain it displays the high quantum yield fluorescence typically observed in aqueous samples.

It has been observed that the degree and kinetics of the activation process are a function of the dielectric of the media. Coulomb's law states that the force between two charged particles is inversely related to the dielectric of the medium:

$$F = \frac{e_1 e_2}{\epsilon r^2} \quad (1)$$

where $e_1$ and $e_2$ are the charged species, $\epsilon$ is the dielectric of the medium, and r is the distance between the charges. As the dielectric is decreased the force between the charges increases as the lack of dipole in the medium prevents dipole solvation of the individual charges.

Figure 2:
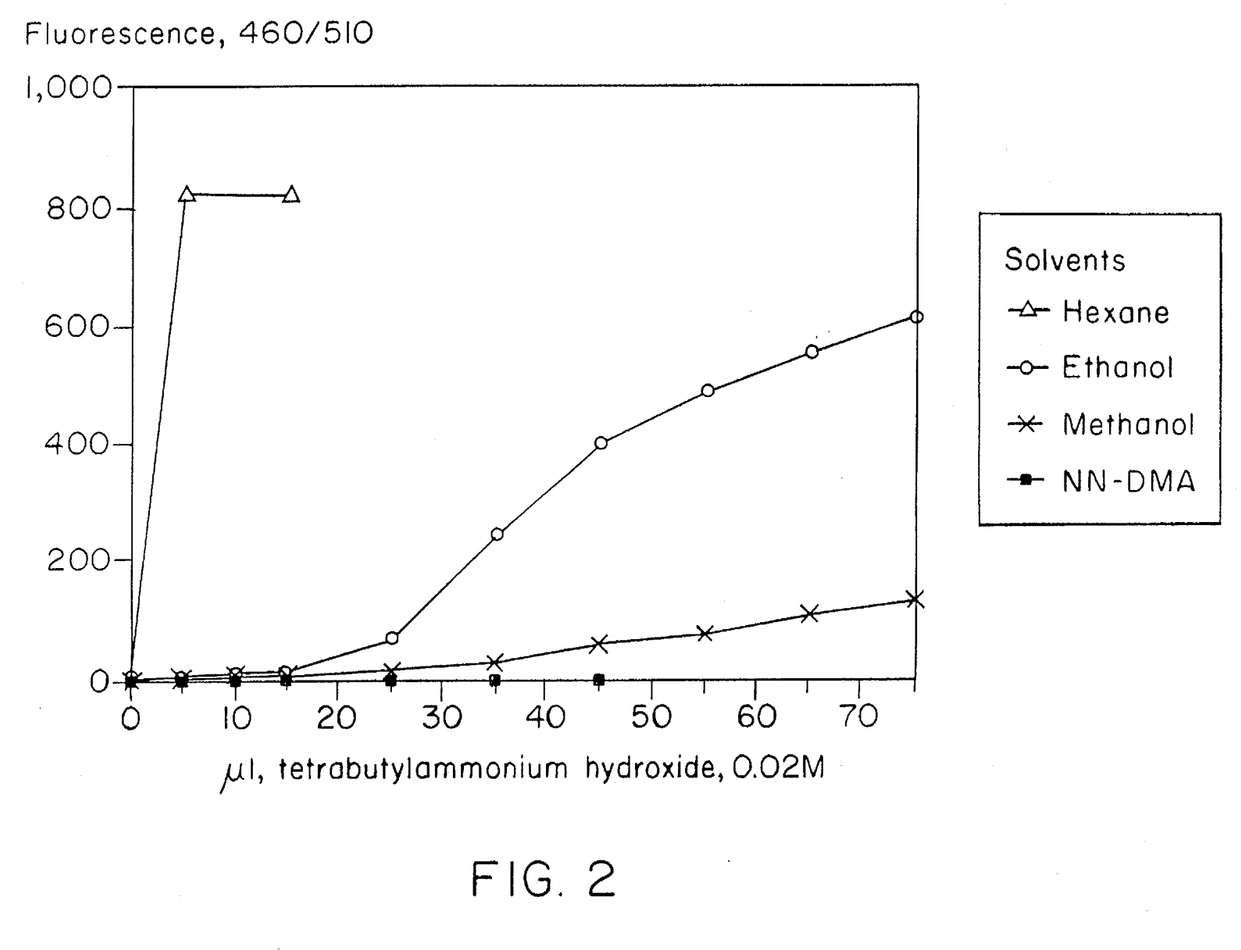
FIG. 2 shows fluorescence activation in solvents with varying dielectric.

The variation in AcOC required for activation of a fluorophore as a function of the dye's solvent can be observed in FIG. 2. In this titration experiment TBAH (0.02 M in ethanol) was titrated into four solutions of HPTS ($5 \times 10^{-7}$ M) in different organic solvents of varying dielectric: 1) hexane, =1.0, 2) ethanol,=24, 3) methanol,=32, and 4) N,N-dimethylacetamide (N,N-DMA),= 38. It can be observed that the complete fluorescence activation in hexane, the lowest dielectric solvent, occurs with only 5 uL of TBAH, giving a final TBAH concentration of 15 0,024 mM, considerably less than a surfactant concentration required for micelle formation (140–0.5 mM, with the higher concentrations required by the surfactants having the shorter alkyl chains.) The titrations that were performed in ethanol and methanol produced a more gradual fluorescence activation and had not gone to completion with addition of 75 ul of TBAH (0.36 mM). The titration carried out in N,N-DMA produced no generation of fluorescence. We concluded from this solvent dependent fluorescence activation that the complex required for fluorescence generation was strongly influenced by the dielectric of the solvent.

Figure 3:
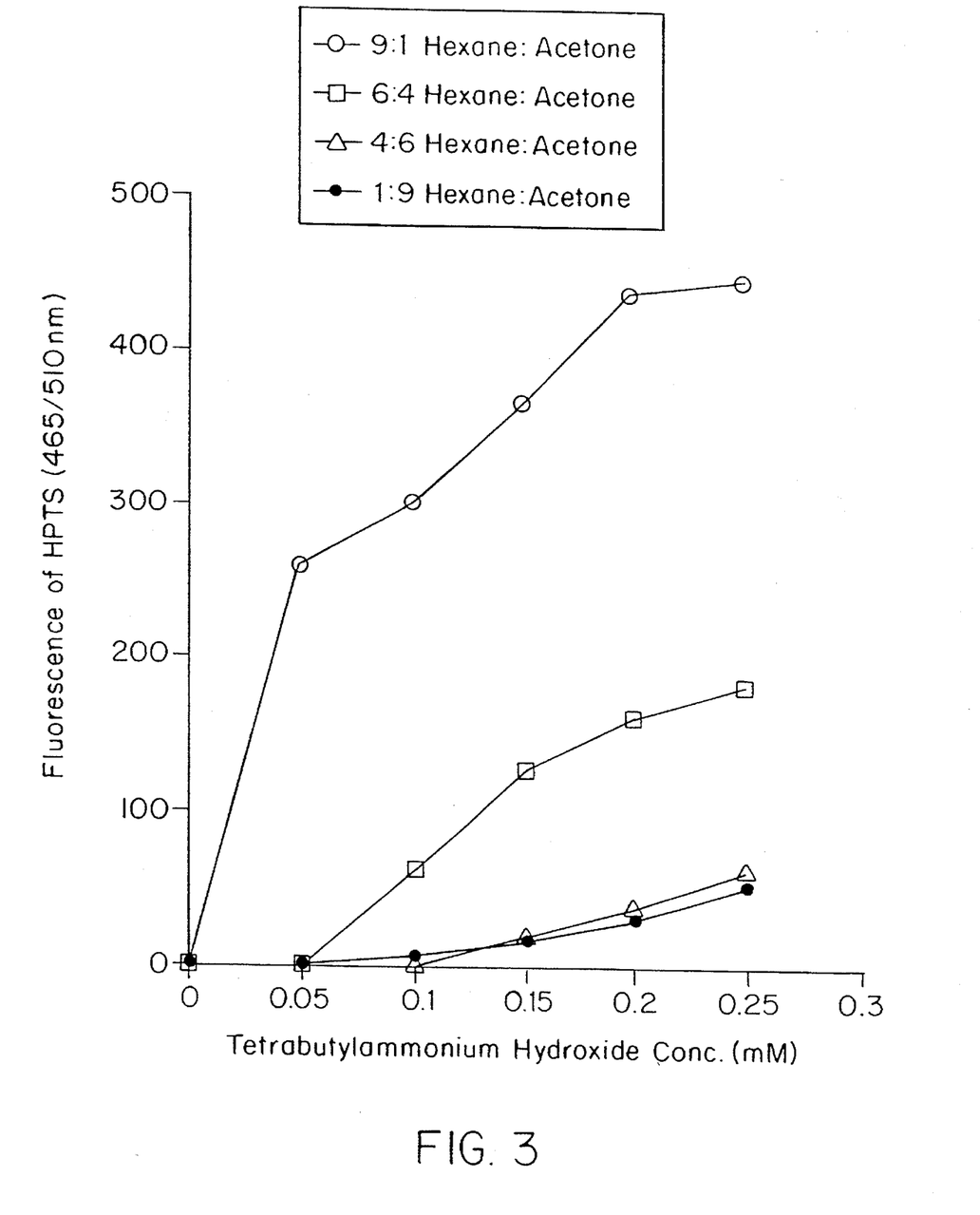
FIG. 3 shows fluorescence activation with varying ratios of hexane and acetone.

Another titration was performed which used different ratios of two solvents of low and mid dielectric so that the fluorophore would be solvated by the same type of solvent molecules without introduction of specific solvent effects such as hydrogen bonding that can occur with alcohols. FIG. 3 shows data for the titration of HPTS with tetrabutylammonium hydroxide, where the relative concentrations of hexane (=1) and acetone (=20) are varied. One observes that the fluorescence is completely quenched in all four solvent ratios, and that the rate and degree of fluorescence activation varies with the relative dielectric, with the lowest dielectric solvent system (9:1, hexane:acetone) most rapidly producing the highest fluorescence intensity with addition of TBAH. In this titration, activated fluorescence was initially observed at a TBAH concentration as low as 0.005 mM, which is again a concentration much lower than that typically reported for micelle formation in surfactant enhanced fluorescence. We attempted the identical titration using the 9:1 hexane:acetone solution of HPTS with the following surfactants: 1) the cationic tricaprylyl monomethyl ammonium chloride, 2) the anionic sodium tridecyl sulfate, and 3) the neutral Triton 100X. Using the surfactant dissolved in butanol as a titrant, we added as much as 3.3 mM surfactant to quenched solutions of HPTS and for all three surfactant titrations zero generation of fluorescence was observed. With the Triton titration, after the final addition of the non-activating surfactant we added 20 ul of $10^{-2}$ M TBAH and saw a pronounced increase of fluorescence signal.

One would assume that the Coloumbic interaction would exist, in a low dielectric media, for all positively charged cationic compounds in low dielectric media with polyanionic dyes. However, we have observed that not all of these compounds perform identically as activators of fluorescence. The most successful quaternary oniums used as AcOCs in our work include tetrabutylammonium hydroxide, hexadecyltrimethylammonium hydroxide, tetraethylammonium hydroxide, tetramethylammonium hydroxide, benzyltrimethylammoniumhydroxide, and benzyltrimethylammonium methoxide. The following onium compounds produced little or no fluorescence when screened in hexane or toluene solutions of dyes: n-hexadecyltributylphosphonium bromide, tetrabutylammonium trifluoromethane sulphonate, tetrabutylammoniumtetraphenyl borate, tetrabutylammonium hydrogen sulphate, tetrabutylphosphonium bromide, and tetrabutylammonium bromide. The component most notably different between the activating and non-activating compounds is the counterion and we believe that the choice of the counteranion may be a critical factor in this method. It is known that halogens can quench fluorescence (Lakowicz, p 258), and it may be that the tetrabutylammonium bromide forms a charge-charge aggregate with the dye that is not fluorescent due to quenching from the high effective concentration of bromide in the polar microdomain.

Comparative titrations to assess the relative activation properties of four of the quaternary ammonium compounds were performed with the following reagents: 1) tetrabutylammonium hydroxide, 2) tetramethylammonium hydroxide, 3) benzyltrimethylammonium hydroxide, and 4) benzyltrimethylammonium methoxide. These compounds were titrated into identical concentrations of HPTS in four different solvents (hexane, toluene, 2-butanol, and methanol), and the fluorescence activation was determined for the four AcOCs in each solvent. It was found that the particular solvent used in the titration was an important factor in the relative performance of these four AcOCs (Table I). The tetrabutylammonium hydroxide titration produced the most relative fluorescence in both hexane ($I_0$=480) and toluene ($I_0$=450). The tetramethylammonium hydroxide generated the most activated fluorescence when the titration was performed in methanol ($I_0$=400), leading to the observation that the solubility of the alkyl ligand in the solvent may be a factor in the success of the aggregation formation. The benzyltrimethylammonium hydroxide produced similar fluorescence in toluene, 2-butanol, and methanol, with the benzyltrimethylammonium methoxide showing a similar pattern, although with superior results in 2-butanol. With these four activation compounds we did not observe identical correlations with the dielectric of the solvent. These results suggest that the solvent solubility of the alkyl ligands on the quaternary ammonium ion may be an important optimization factor; they may determine the capacity for an alkyl ammonium ion to partition into a particular solvent system.

It has also been observed during these titration studies that the solvent used for the AcOC dilution was a factor in the degree of fluorescence generation. For example, when the AcOC was dissolved in methanol and the dye was dissolved in butanol the dye was extracted into the AcOC/MeOH phase and fluorescence was observed only in the very small, immiscible volume of the addition, and not in the bulk solution. Upon changing the AcOC solvent to one that was miscible with butanol, such as ethanol, we observed generation of fluorescence in the bulk dye/butanol solution. Superior results were often obtained when the dye solvent and AcOC solvent were the same.

Quaternary ammonium hydroxides have been used as titrants in nonaqueous media (Harlow, G. A., Noble, C. M., Wyld, G. E. A., Analytical Chemistry, 28,787, 1956) and it has been suggested that we are observing a titration of a pH sensitive fluorophore into a deprotonated high quantum yield state. However, HPTS has a high quantum state in both its protonated and deprotonated forms and in the absence of AcOC we observe neithor form of fluorescence when the dye is in a quenching media. Also, we have successfully used this method to activate the fluoresence of dyes which are not pH sensitive and therefore not capable of proton titration: pyrenetetrasulphonate and ethylenediaminepyrenetrisulphonate. However, HPTS is activated in its basic form as we always observe the generation of the excitation spectrum in the 455–465 nm region, and it is probable that the dye is being deprotonated by the hydroxide and methoxide counterion on the quaternary ammonium ions that successfully activated fluorescence. These experiments suggest that the AcOC can interact with the fluorophore in both a general and a specific manner. The general interaction produces the charge-charge aggregate altering the microenvironmental polarity of the dye, and the specific interaction produced by the counterion can modulate the properties of the activated fluorescence, or in the case of certain counterions, quench the activated fluorescence.

Figure 4:
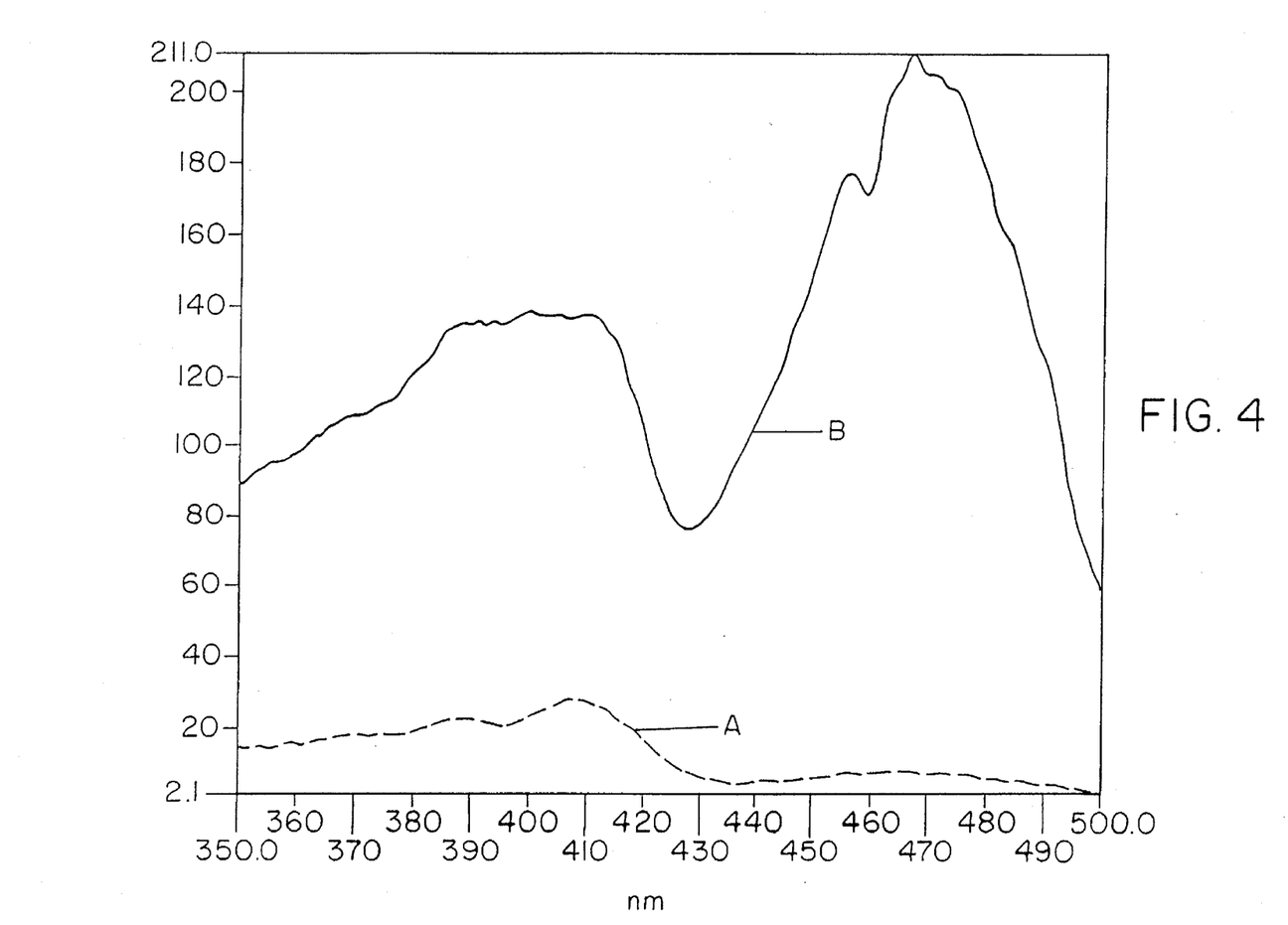
FIG. 4 shows comparative fluorescence excitation spectra of HPTS in toluene and ethanol and the same solution with the ammonium copolymer added.
Figure 5A:
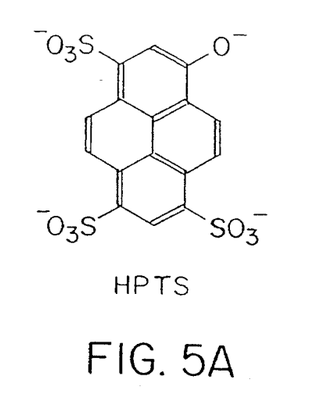
FIG. 5 shows examples of polyanionic fluorophores which can be activated by AcOC compounds.
Figure 5B:
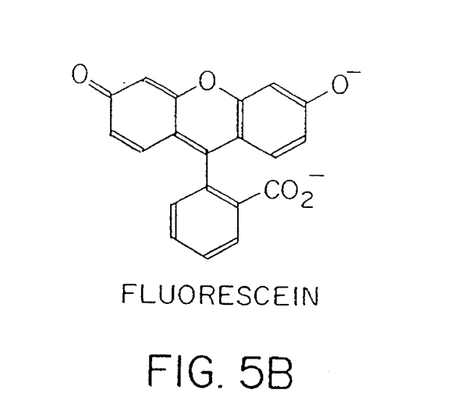
Figure 5C:
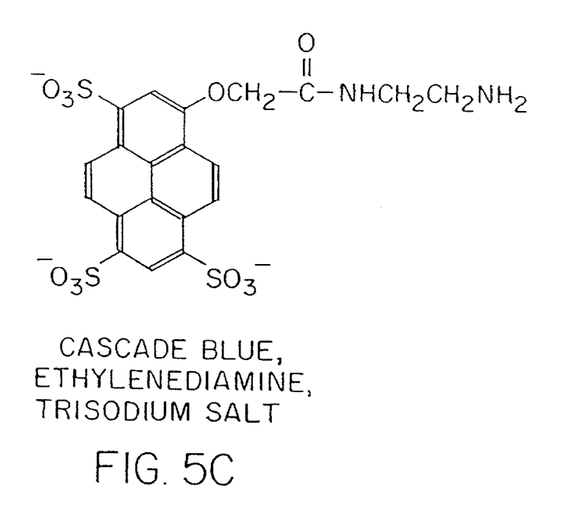
Figure 5D:
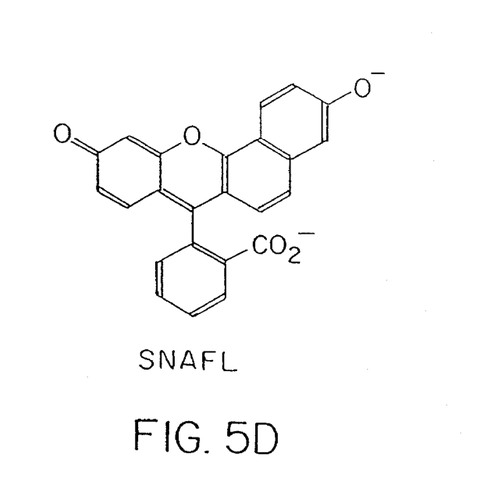

Activation of fluorescence in solution with a copolymer prepared from methyl methacrylate and methacrylamidopropyl trimethyl ammonium chloride (MAPTAC) has also been demonstrated. Since the polymer contains a trimethylpropylammonium group, it has a functionality similar to the cationic component in the TBAH and other AcOCs under discussion. FIG. 4 shows (a) the excitation spectra of a solution of HPTS, $2\times10^{-6}$ M in toluene: ethanol (8:2) and (b) the same solution after addition of the ammonium copolymer (0.08%). The MAPTAC activated fluorescence differed from the TBAH activated fluorescence as the excitation bands indicate more presence of the acidic form (402 nm) of the dye than observed with the TBAH activated fluorophore although the basic form is in excess. It was also observed that when the polymer settled in the test tube it was fluorescent green, indicating complexation with the basic form of the dye. The use of a polymer as the fluorescence activator is of interest as this offers the potential for preparing fluorescent coatings where the activator and polymer component are combined into a single reagent. If the polymer were also to contain an additional functional group suitable for covalent immobilization, one could thus prepare a fluorescent coating covalently coupled to the substrate. The MAPTAC polymer has also demonstrated fluorescence activation in the solid phase, both as the activator component added to another polymer solution, and when used alone, serving as the activator and the sole membrane polymer component.

Activation of fluorescence on the surface of a strong anion exchange resin (Dowex 19880) has also been demonstrated. When this resin was added to a non-fluorescent solution of HPTS dissolved in hexane, the resin became highly fluorescent green, the color consistent with the activation of HPTS in its basic structure. The resin contains an ammonium group, and the generated fluorescence was due to complex formed between the ammonium cation and the negatively charged dye, with neutralization of the quenching effect of the nonpolar solvent. After removal of the resin from the solvent, the resin remained fluorescent green, indicating that one can use this method to deposit fluorescent coatings onto ammonium derivatized surfaces from low dielectric solvents.

An important component of this invention is the identification of a class of dyes which are successfully converted to high quantum yield dyes in an environment where their fluorescence would be normally quenched. The main requirements for this class of dyes are: 1) the presence of negatively charged substituents on the structure of the dye, 2) a high quantum yield in water, 3) a low quantum yield in nonpolar media, 4) solubility in a nonpolar solvent, and 5) the dye, if pH sensitive, must have at least one other position of negative charge on the molecule's structure, other than the postion of deprotonation.

Titration experiments were performed on dyes that were dissolved in hexane or toluene, and then titrated with tetrabutylammonium hydroxide. The six dyes that were titrated from a quenched state to a high quantum fluorescence state in the low dielectric media were: fluorescein, 2',7'-dimethyl rhodol (DM-NERF from Molecular Probes), seminaphthofluorescein (SNAFL from Molecular Probes), hydroxypyrenetrisulphonate (HPTS), ethylenediaminepyrenetrisulphonate trisodium salt (available as CASCADE BLUE ethylenediamine trisodium salt, product C-621 from Molecular Probes, Inc.), and pyrenetetrasulphonate. These dyes are all polyanionic, and structures of several of them are shown in FIG. 5. Typically these dyes are highly fluorescent (have a high quantum yield) when measured in aqueous solutions. It is not required that the dye be pH sensitive for fluorescence activation with an AcOC, which is demonstrated by the ethylenediamine-pyrenetrisulphonate and pyrenetetrasulphonate titrations as neither of these dyes are pH sensitive. Other pyrenetrisulphonate derivatives, such as acetyl azide, aminoethyl p-azidobenzamide, cadaverine, or hydrazide are also usable herein as activatable fluorescent dyes.

Clearly, not all fluorescent dyes will be activated by this method. Dyes that were uncharged, such as pyrene and neutral red displayed no quenching in the nonpolar solvent and were unaffected by addition of an AcOC. The pH sensitive hydroxypyrene was not quenched in the nonpolar solvent and the addition of TBAH caused a loss of fluorescence which is consistent with the dye's acid/base characteristics; in a basic buffer the deprotonated structure has the low quantum yield, and in this experiment the TBAH performed as a deprotonating base in the hexane solution.

Figure 6:
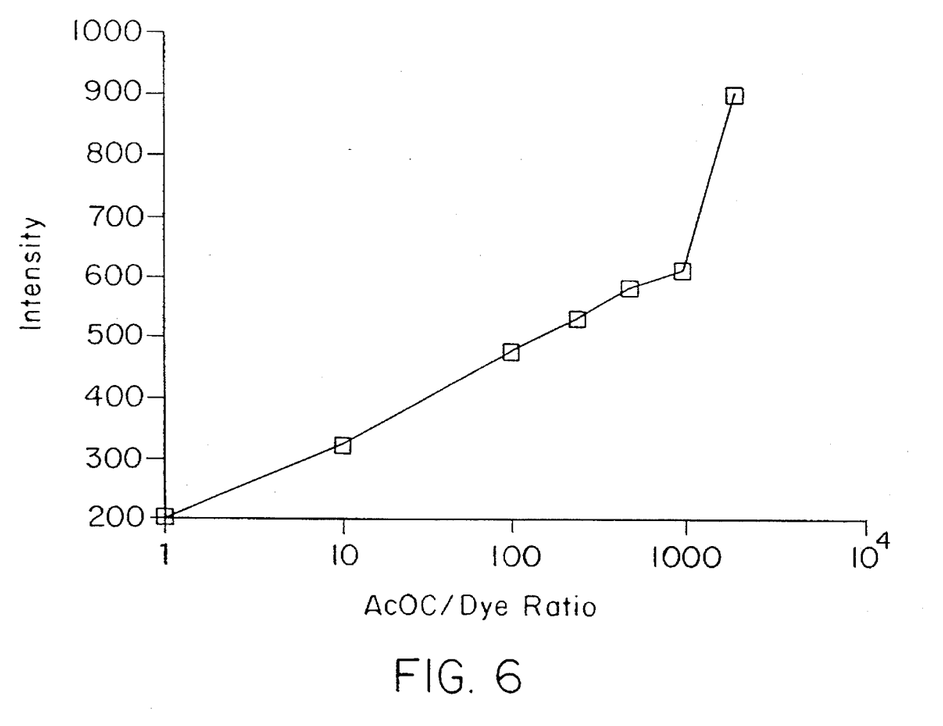
FIG. 6 shows the fluorescence intensity of polymer membranes as a function of the molar ratio of AcOC to dye.

This method has also been used to activate fluorescence in polymer coatings prepared with low dielectric solvents, such as a polystyrene coating prepared in toluene. Table 2 shows the comparative fluorescence of coatings made from polystyrene/fluorophores and polystyrene/AcOC activated fluorophores. The controls prepared with no activator displayed little or no fluorescence, while those with activator showed significantly higher fluorescence. The coatings were prepared by spinning a polymer/dye solution onto a glass surface and then allowing evaporation of the solvent in air. The fluorescent coating is stable and dependent on the concentration of AcOC in the formula. FIG. 6 shows the fluorescence dependence on AcOC concentration in solution used for coating a series of substrates that differed only in their concentration of activator, with the dye and polymer concentrations being identical. With increasing AcOC concentration the fluorescence of the coating increases. Again, the fluorescence was measured on the surface of the coated substrates after the solvent was evaporated and the polymer was in an effectively dry state.

Another important aspect of the invention is the use of a low dielectric media as the solvent or solid support for the activated fluorescence complex. Low dielectric solvents are organic solvents having little or no dipole moment, such as hexane or butane as well as certain aromatic solvents such as benzene and toluene. Polymers that are soluble in these low dielectric solvents are also regarded as low dielectric media, and they retain their nonpolar microenvironmental nature after the solvent has evaporated. A charged fluorescent dye, when dissolved in a low dielectric solvent or polymer, will experience a change in the photophysical properties, such as a bathochromic or hypsochromic shift, or a complete quenching of the fluorescence, depending on the nature and number of the charges on the dye as well as the difference between the dipole of the ground state and the dipole of the excited state. This phenomenon was observed with the polyanionic fluoropohores described in this invention. This invention is not confined to a precise cutoff in the dielectric range as the particular dielectric dependency of different dyes will vary. We direct this invention to fluorescent dyes that experience a loss of quantum yield at a given dielectric of the media for the particular dye, that being the dielectric where photon emission decreases or does not occur.

As stated this invention also describes a method of activating fluorescence in polymer coatings wherein the fluorescence would normally be quenched without the addition of an AcOC. Again the precise dielectric range of the polymer can not be defined but will be a function of the dye that is included in the formula. If the dielectric is such that the charge-charge interaction of the AcOC and dye is favored, fluorescence activation will occur with addition of the activation compound and be sustained after evaporation of the solvent.

Polymers that may be suitable for this invention and used as a sensor coating and/or a cover membrane over the sensor coating include but are not limited to the following list: poly(dienes), such as poly(1,3-butadiene), poly(butadiene-coacrylonitrile), poly(dimethylbutadiene), and poly(isoprene); poly (alkenes), such as poly(ethylene), poly(isobutane-coisoprene), poly(4-methyl pentene), poly(propylene), poly(ethylmethacrylate), poly(styrene), poly(tetrafluoroethylene), poly(vinyl alcohol), poly(vinyl chloride), and poly(oxymethylene); cellulose and cellulose derivatives, such as cellulose hydrate, cellulose acetate, cellulose nitrate, ethyl cellulose, and ethyl methacrylate; poly (methacrylates) such as poly (methyl methacrylate) and poly(ethyl methacrylate); as well as poly(siloxanes), poly(esters) and poly(carbonates).

Another important feature of the invention is the ability to use these low dielectric coatings in aqueous samples without the loss of dye from the membrane as the low dielectric polymers tend to be hydrophobic. However, one could modify diffusion or permeable dependent response properties by addition of a second coating over the polymer containing the activated fluorescence. This second coating could be prepared from the same polymer, or from a polymer of different structure but compatible with the first coating to facilitate deposition. Furthermore, it is possible to combine the activating compound and fluorophore with the solid material (e.g., low dielectric polymer or glass) when the solid material is being cast so that these components are incorporated into the solid material.

Although the polymers with the activated fluorescence can be used as fluorescent coatings the novel analytical application is their use as transducer coatings for optical sensors. We have observed that the fluorophores, once activated in the polymer, not only have their high quantum yield restored, but also exhibit any specific chemical sensitivity for which the dye is characterized. For instance, if a dye has a pH dependent acid/base equilibrium, this property will be intact in the restored fluorescence, but will measure the microenvironmental pH. We can indirectly test the pH sensitivity by introducing an analyte that can pass through the polymer and become solubilized in the polar microdomain of the AcOC/dye aggregate. Within these microdomains the dye experiences a microenvironment similar to that of water and can function as an analytical reagent characteristic of the dye in water. These reactive microdomains are now dispersed throughout the polymer membrane that serves as a support for the transducer. Since the polymer is hydrophobic the sensor response will be due only to an analyte that can permeate the polymer, such as a vapor or gas.

The traditional method of preparing an optical $CO_2$ sensor has been based on the Severinghaus model (Severinghaus, J. W.; Bradley, A. F. J. Appl. Physiol. 1958, 13, 515) where one has a transducer layer containing a pH sensitive fluorophore or chromophore, which is soaked in a $NaHCO_3$ solution, and then coated with a hydrophobic cover membrane material, such as a siloxane based polymer (Munkholm, C., Walt, D. R., Milanovich, F. P., Talanta, 35(2), 109–112, 1988) The exposure to $CO_2$ produces a quantifiable change in fluorescence due to $CO_2$ diffusing into the sensor membrane and altering the microenvironmental pH with the accompanying change in the fluorescence of the pH sensitive fluorophore. A difficulty inherent with Severinghaus sensors is their potential to fail due to pinhole leaks in the cover membrane. Sensors prepared by the instant invention will also provide quantitative measurements of $CO_2$ levels via a pH sensitive modulation of the microenvironment of the activated fluorophore. Since these sensor microenvironments are dispersed throughout the low dielectric medium, preparing such a sensor requires only a single application of the membrane material, and this single membrane configuration makes the problem of pinhole leaks irrelevant. These sensors have been used in liquid samples for measuring $CO_2$ continuously over a period of 50 hours, showing only gradual loss of intensity due to photobleaching. The sensors were not responsive to changes in the bulk pH, indicating that the transducer microdomains were sequestered from the sample. This sensor has been used in a system which measures reflected surface fluorescence as well as in a system measuring an evanescent wave signal. Other gases which (Wolfbeis, O. S., Posch, H. E., Analytica Chimica Acta, 185, 321–327, 1986) (Lopez, M. E., Rechnitz, G. A., Analytical Chemistry, 54, 1976–1980, 1982.) could be the basis of an analytical sensor prepared via the AcOC sensor method.

Oxygen is an analyte frequently measured via optical methods such as fluorescence quenching. Fluorophores that meet our requirements for AcOC activation and that also have a fluorescence lifetime suitably long enough for quantitation of fluorescence quenching as a function of $O_2$ concentration would be candidates for an AcOC sensor prep.

An advantage of optical sensors is their ability to resolve information from different analytes via their discrete wavebands. In this way one could couple two sensors together in the same membrane, but collect the readout information at separate wavelengths. The disclosed invention would enable one to prepare such sensor configurations in a single coat. The sensor microdomains would be populated by multiple transducers but the chemistry and signal processing would be conducted as if the sensors were in separate layers.

Using this method one can prepare extremely thin sensor films having a detectable level of fluorescence. Such thin films may provide an unusually rapid response time and be ideal for coating planar sensors used in evanescent wave methods of detection where one wants a fluorescent coating to be within the same dimensions as the propagating wave. Sensors prepared with this method will not be affected by pinhole leaks as the sensor material is continuous in the coating. These sensor films may also have a longer shelflife due to their lack of an aqueous layer.

EXAMPLES

The following examples illustrate the invention but are not intended to limit the usefulness thereof.

Examples 1–4: Fluorophore activation with quaternary ammonium ions

As discussed above, a particular dye's ability to be used in this system of fluorescence activation requires that the dye be polyanionic and have a high quantum yield in water and a low quantum yield in a low dielectric media. It should be possible to select suitable dyes for this method by use of existing spectral data base, since it has been found that all dyes meeting this criteria, when dissolved in a media that quenches the fluorescence, are activated by addition of specific quaternary ammonium ions. The quaternary ammonium ions that have successfully activated fluorescence have had either a hydroxide or a methoxide counterion, and have been dissolved in solvents miscible with the solvent used for the fluorophore.

Example 1

A sample containing fluorescein dissolved in a low dielectric solvent, toluene, was irradiated in a fluorimeter (Perkin-Elmer, LS-50) to establish the very low or absent baseline fluorescence. The excitation was 488 nm and the fluorescence measured at 530 nm using a 530 nm filter on the emission beam, $I_0=2$. A quaternary ammonium ion, tetrabutylammonium hydroxide, was diluted with a solvent, butanol, which is miscible with the solvent used for the dye sample. The quaternary ammonium solution was then titrated into the fluorescein solution until the monitored fluorescence emission was generated to a stable level, $I_1=289$. (In the examples, $I_0$ refers to fluorescence of the quenched state of the flourophore, and $I_1$ refers to the fluorescence of the activated state of the fluorophore.)

Example 2

Fluorescence activation of fluorescein was compared in four solvents by preparing $5\times10^{-7}$M concentrations of the dye in hexane, toluene, tetrahydrofuran, and 2-butanol. Emission spectra were taken with 488 nm excitation. Nearly completely quenched fluorescence was observed in hexane, toluene, and tetrahydrofuran; in 2-butanol $I_1=250$. The solutions were titrated with 0.01 M tetrabutylammonium hydroxide dissolved in ethanol until a stable level of fluorescence was generated. The four systems required varying amounts of activator and also yielded different levels of fluorescent signals (Table 3). Of these four solvents, hexane has the lowest dielectric and the fluorescein/hexane solution produced the largest increase of fluorescence with the lowest concentration of TBAH required for full activation. (Note that the 2-butanol was a special case, because it was not fully quenched.)

Example 3

Figure 7:
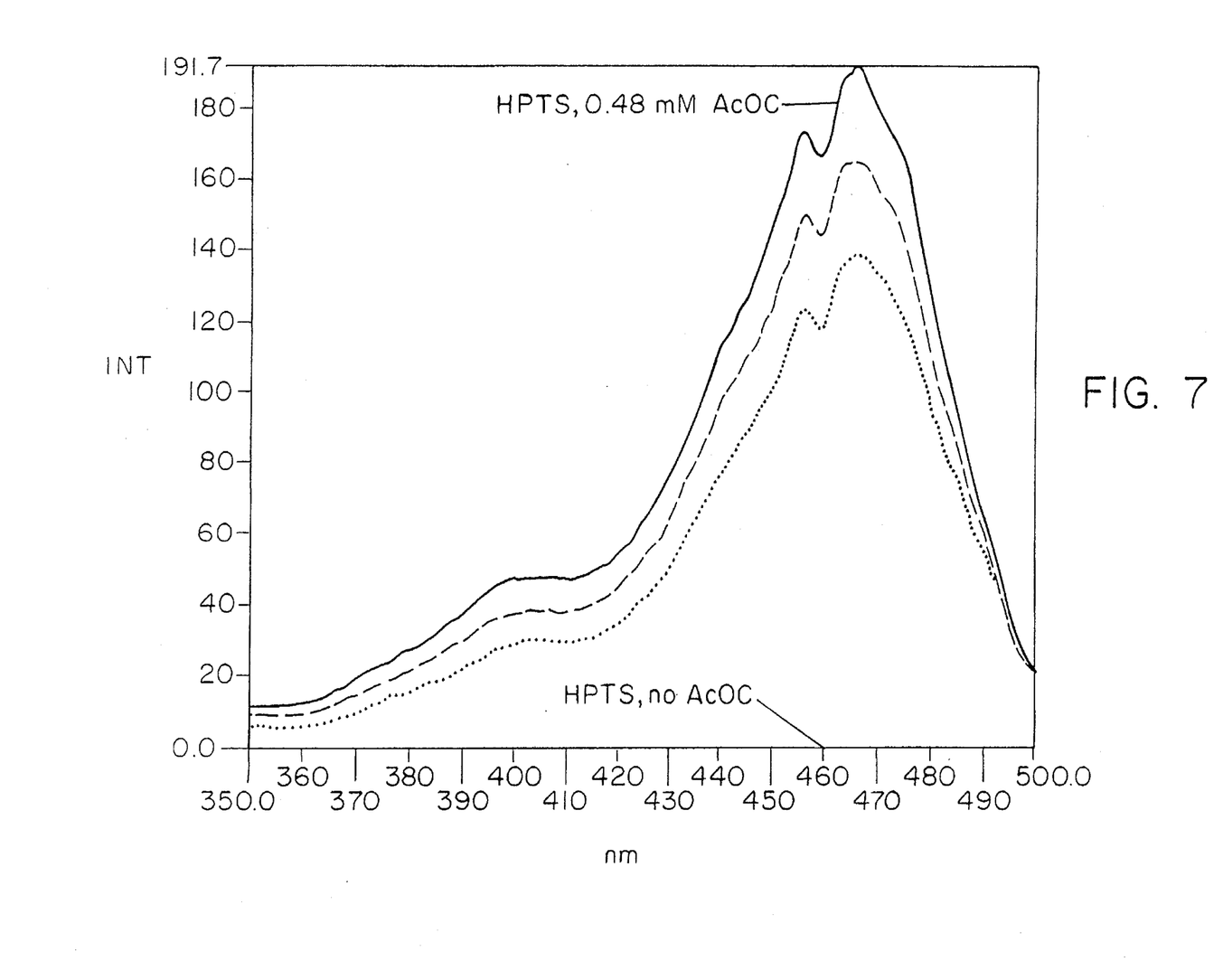
FIG. 7 shows comparative fluorescence excitation spectra of HPTS with titration of AcOC into the toluene solution.

Hydroxypyrenetrisulphonate (HPTS) was dissolved in a low dielectric solvent, toluene, and an excitation spectrum was generated between 350 nm and 500 nm, using 510 nm emission, to establish the baseline fluorescence, $I_0=1$ at 462 nm. A quaternary ammonium ion, tetrabutylammonium hydroxide, was diluted to 0.01 M with 2-butanol, which is miscible with the solvent used for the dye sample. The quaternary ammonium solution was then titrated into the HPTS solution until the monitored fluorescence excitation was generated to a stable level, $I_1=192$ at 462 nm. With HPTS titrated with tetrabutylammonium hydroxide, the activated excitation energy maximum was observed at 462 nm, consistent with the dye being in the basic form. (FIG. 7 ).

Example 4

Ethylenediamine-pyrenetrisulphonate was dissolved in toluene to give $5\times10^{-7}$ M. An excitation spectrum was generated between 300 nm and 410 nm, using 423 nm emission, to establish the baseline fluorescence. At 378 nm and 399 nm excitation maxima, almost zero fluorescence was observed. Addition of 0.250 ml tetrabutylammonium hydroxide (0.01 M, 2-butanol) generated 650 fluorescence units, with peaks occurring at 378 nm and 399 nm, where the excitation maxima are reported in aqueous media. When the same titration was performed with ethylenediamine-pyrenetrisulphonate dissolved in 2-butanol, a 0.01 ml addition of the same AcOC generated fluorescence intensity that was extremely off scale, estimated at 2000+ relative fluorescence units. This dye is pH insensitive.

Examples 5–6: Fluorophore activation by a polymer containing a quaternary ammonium functional group The addition of MAPTAC, a copolymer containing a quaternary ammonium group, also activated the fluorescence of a quenched fluorophore in a low dielectric solvent. The use of the polymer as the fluorescence activator resulted in more of a mixture of acidic and basic forms of the activated dye.

Example 5

HPTS was dissolved in a low dielectric solvent system of toluene: ethanol, 6:4. An excitation spectrum was generated between 350 nm and 500 nm, using 510 nm emission, to establish the baseline fluorescence, $I_0=21$ (405 nm) and $I_0=8$ (465 nm). A 5% (w/v) solution of MAPTAC polymer dissolved in ethanol was titrated into the HPTS sample until a stable level of fluorescence was generated, $I_1=140$ (405 nm) and $I_1=211$ (465 nm). The excitation bands appeared at 405 nm and 465 nm, indicating that a mixture of acidic and basic forms of the dye were present in the activated state.

Example 6

HPTS was dissolved in hexane and an excitation spectrum was generated between 350 nm and 500 nm, using 510 nm emission, to establish the baseline fluorescence, $I_0=5$ (405 nm) and $I_0=5$ (465 nm). A 5% (w/v) solution of MAPTAC polymer dissolved in ethanol was titrated into the HPTS sample until a stable level of fluorescence was generated, $I_1=250$ (405 nm) and $I_1=39$ (465 nm). Since the more intensely activated excitation band appeared at 405 nm, it was indicated that predominately the acidic form of the dye was activated. When this titration was performed in ethanol, the basic form of the activated dye was in excess, $I_1=200$ (405 nm—protonated form) and $I_1=598$ (465 nm—deprotonated form).

Example 7

Fluorophore activation with an anion exchange resin

A surface containing an ammonium group has also been used to demonstrate activation of a quenched fluorophore in a low dielectric media. In this example the dye is extracted from the solution by complexation with the solid resin.

HPTS ($10^{-5}$M) was dissolved in hexane, and to this solution approximately 250 mg of DOWEX 19880 Anion Exchanger was added. After vortexing, the resin was removed from the dye solution by filtration and rinsed with hexane. By observation under an ultraviolet light the resin appeared fluorescent green, the color typical of HPTS in the basic form. To confirm the presence of activated fluorophore a spectral measurement was made by immobilizing the resin on a coverslip with freshly applied polystyrene. After the polymer dried the surface fluorescence of the coverslip was tested in the LS-50, and fluorescence was observed at the 465 nm excitation band, consistent with HPTS in the basic form.

Examples 8–13: Fluorophore activation in a polymer membrane, using a quaternary ammonium ion compound The addition of an AcOC to a polymer/dye solution dissolved in a low dielectric solvent produced activation of fluorescence in the liquid sample. When the solution was applied to a glass coverslip with evaporation of the solvent, the polymer coating was highly fluorescent.

Example 8

Fluorescein (2 mg) and tetrabutylammonium hydroxide (1.5 ml, 1.0 M) were dissolved in 10 ml 2-butanol. A polystyrene solution was prepared by dissolving 0.7 g polystyrene in 10 ml toluene. A 5 ml aliquot of polymer solution was combined with 0.91 ml dye/TBAH solution. This solution was highly fluorescent in the test tube. The polymer/dye solution was then spincast onto glass substrates, and the coating that resulted was fluorescent, $I_1=270$, displaying the same spectral properties of fluorescein as observed in an aqueous system, excitation maximum=490 nm and emission maximum= 520 nm.

Example 9

A polystyrene solution was prepared by dissolving 0.6 g polystyrene in 10 ml toluene. A solution of $10^{-3}$ M HPTS was prepared with 2-butanol. The HPTS solution (1 ml) was added to the 10 ml of polymer. After mixing, a 3 ml aliquot of polymer/dye solution was removed and mixed with 0.082 ml 1.0 M tetrabutylammonium hydroxide. The activated and nonactivated polymer/dye solutions were then applied on glass coverslips via spin coating. The polymer/dye, without AcOC, produced a coating with little fluorescence, $I_0=10$, and the polymer/dye/AcOC solution produced a coating that was fluorescent, $I_1=380$.

Example 10

A methyl cellulose acetate solution was prepared by dissolving 0.5 g polymer in 5 ml toluene: ethanol (4:1). A solution of $10^{-2}$ M HPTS was prepared with methanol. The HPTS solution (0.5 ml) was added to the polymer solution. With addition of 0.03 ml 1.0 M tetrabutylammonium hydroxide the solution became bright fluorescent green. The polymer solution was applied to a glass coverslip and after evaporation of solvent the polymer coating remained fluorescent.

Example 11

An 8% solution of a proprietary acrylate polymer was prepared by dissolving 0.4 g in 5 ml toluene. To the polymer solution 0.25 ml HPTS ($10^{-3}$M, 2-butanol) was added and 1 ml of the polymer/dye solution was removed as a control. To the remaining 4 ml of polymer/dye, 0.060 ml 1.0 M tetrabutylammonium hydroxide was added, and the solution became bright fluorescent green. Both the fluorescent and control solutions were spincoated onto glass substrates, and after evaporation of the solvent the polymer with the activated fluorescence remained highly fluorescent, $I_1=390$, (465 nm excitation, 510 nm emission) and the coating prepared with the control had little fluorescence, $IO=9$.

Example 12

A 6% solution of ethyl cellulose was prepared by dissolving 0.6 g in 10 ml of toluene:ethanol, 8:2. To the polymer solution 1.0 ml HPTS (10–3 M, methanol) was added. Two ml polymer/dye solution was removed as a control. To the remaining polymer/dye 0.283 ml 1.0 M tetrabutylammonium hydroxide was added, and the solution became bright fluorescent green. Both the fluorescent and control solutions were spincoated onto glass substrates, and after evaporation of the solvent the polymer with the activated fluorescence remained highly fluorescent, $I, = 560$ (465 nm excitation, 510 nm emission) and the coating prepared with the control was not very fluorescent, $I_0=21$.

Example 13

A 5% solution of polystyrene was prepared with toluene. A $10^{-3}$ M solution of pyrenetetrasulphonate was prepared by dissolving 12.2 mg in abs. ethanol. To 2 ml of polymer solution was added 0.2 ml pyrenetetrasulphonate and 0.06 ml 1.0 M tetrabutylammonium hydroxide, producing a fluorescent solution. A control solution was prepared with no AcOC. Both the fluorescent and control solutions were spincoated onto glass substrates, and after evaporation of the solvent the polymer with the activated fluorescence remained highly fluorescent, $I_1$=742 (excitation, 375 nm and emission, 404 nm) and the coating prepared with the control had little fluorescence, $I_0$ =21.

Examples 14–15: Fluorophore activation in a polymer coating containing a quaternary ammonium functional group Fluorescence activation of a quenched fluorophore has been achieved in a polymer coating by inclusion of the copolymer with a quaternary ammonium functional group, referred to as MAPTAC.

Example 14

A 10% MAPTAC solution was prepared with 95% ethanol. To a 2 ml polymer solution 0.1 ml HPTS ($10^{-5}$M, ethanol) was added and the solution became intensely fluorescent, as observed in the test tube. The polymer/dye solution was applied to a glass coverslip, and the solvent evaporated overnight. Fluorescence was measured; $I_1$=473, (405 nm excitation, 510 nm emission) and $I_1$=262 (455 nm excitation, 510 nm emission). With a control solution of HPTS in ethanol the fluorescence measurements were: $I_0$=22 (402 nm excitation), and $I_0$=4 (455 nm excitation).

Example 15

A 2% solution of ethyl cellulose was prepared with toluene:ethanol, 6:4, and HPTS was added to give a final concentration of $2\times10^{-6}$M. A 10% MAPTAC solution was prepared with ethanol, and titrated into the ethyl cellulose solution until the fluorescence was fully activated. The polymer/dye solution was applied to a glass coverslip, and the solvent evaporated overnight. An excitation spectrum was generated between 350 nm and 500 nm, using 510 nm emission. At 402 nm the excitation intensity=623, and at 465 nm the excitation intensity=175. A control solution of ethyl cellulose/HPTS displayed little fluorescence.

Examples 16–19: Preparation of $CO_2$ sensors with quaternary ammonium ion activated fluorescence Several of the activated fluorescent pH-sensitive dye/polymer formulations have been been spincoated as membranes on a glass substrate, and have been successfully demonstrated as quantitative $CO_2$ sensors, in both liquid and gas phase testing.

Example 16

Using the formulation described in Example 8, sensors were prepared by spincoating the polymer/dye solution onto glass coverslips that were coated with Glass Clad, a proprietary silanization reagent that renders glass hydrophobic. The sensors were cured at room temperature and the solvent evaporated overnight. For $CO_2$ testing, the sensor was inserted into the Perkin-Elmer LS-50 fluorimeter, and was exposed to different concentrations of gaseous $CO_2$ passed through the flow cell on line with the sensor. The sensor responded reversibly and reproducibly to variations in $CO_2$: Air (0.03% $CO_2$), $I_1$=268, 3% $CO_2$ $I_1$=252, 5% $CO_2$, $I_1$=242, and 7%, $I_1$=230.

Example 17

Figure 8:
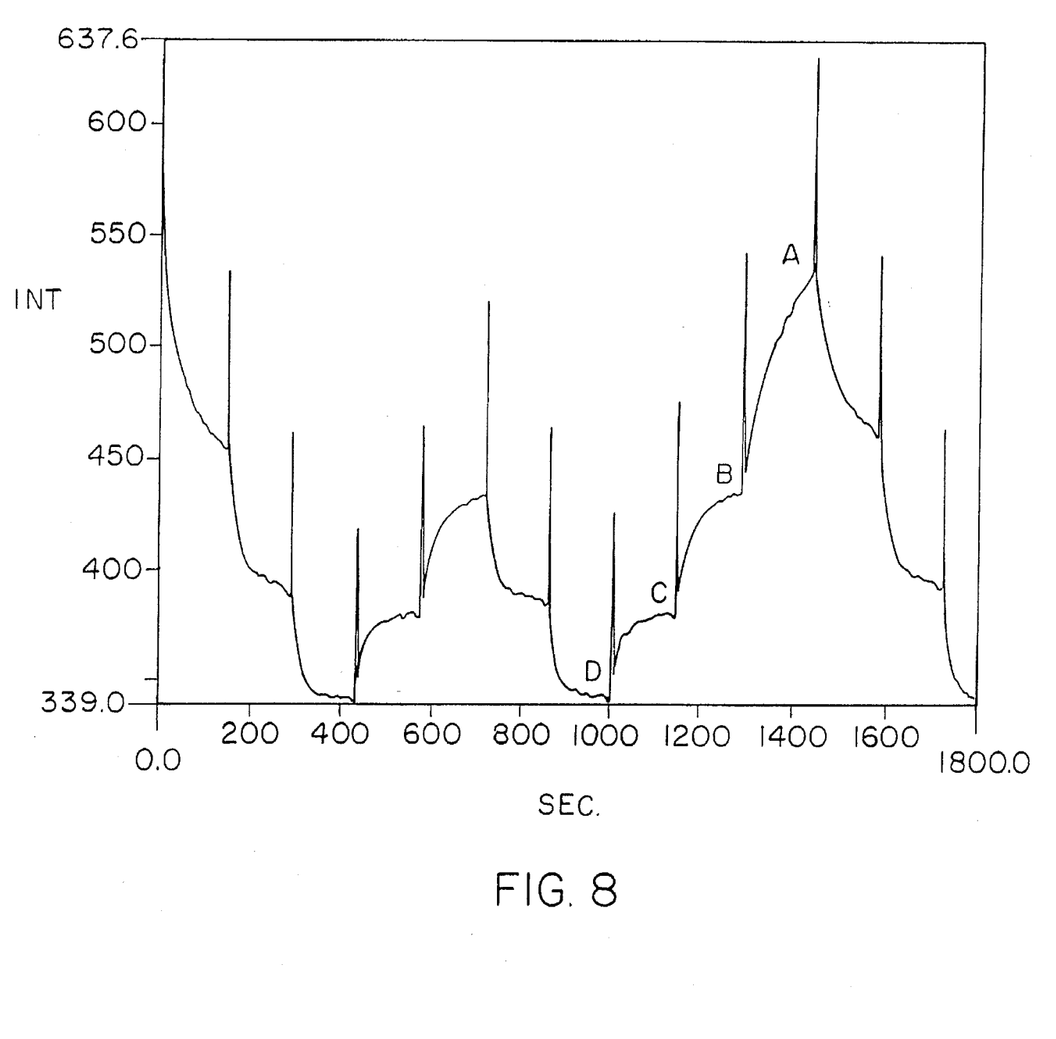
FIG. 8 shows the $CO_2$ response of a sensor membrane.

A 5% solution of ethyl cellulose was prepared with toluene: ethanol, 9:1. An HPTS solution prepared with butanol was added to the polymer to give a concentration of $1\times10^{-7}$ M and hexadecyltrimethylammonium hydroxide was added to give $1\times 10^{-5}$ M. The intensely fluorescent solution was spincoated onto glass coverslips treated with Glass Clad silane reagent, and the sensors were allowed to cure overnight in ambient conditions. The sensor was tested in a fluidics system, and it demonstrated a reversible, quantitative response to tonometered $CO_2$ buffers for a period exceeding 100 hours. A representative 30 minutes of testing is displayed in FIG. 8, with the fluorescence levels measuring these concentrations of $CO_2$: A) 0.03%, B) 2.66%, C) 5.33%, and D) 8.33%.

Example 18

Using the formula described in Example 9, sensors were prepared as described in Example 16, and tested on the same equipment using buffers tonometered with varying concentrations of $CO_2$. A calibration curve was generated by plotting the fluorescence response of the sensor in standard concentrations of $CO_2$ tonometered buffers. The fluorescence of the sensor was then determined when inserted in various samples containing unknown amounts of $CO_2$, and the concentration of $CO_2$ therein was then determined by reference to the calibration curve. The sensor displayed reversible and well resolved measurements of $CO_2$: water(0.03% $CO_2$), $I_1$=525; 2.66% $CO_2$, $I_1$=450; 5.33% $CO_2$, $I_1$=390; and 8.66% $CO_2$, $I_1$= 321. The sensor was tested for several hours of continuous cycling with the $CO_2$ samples.

Example 19

The same sensor preparation described in Example 18 was used to make sensors. After the deposition and drying of the polymer/dye layer, an additional coating of 5% polystyrene in toluene was applied to the sensor, as a protective layer. In liquid testing, the sensor displayed reversible, rapid, and well resolved measurements of $CO_2$: water (0.03% $CO_2$), $I_1$=575; 2.66% $CO_2$, $I_1$=440; 5.33% $CO_2$, $I_1$=350; and 8.66% $CO_2$, $I_1$= 310.

Examples 20–21: Preparation of $CO_2$ sensors with quaternary ammonium derivatized polymer The MAPTAC polymer which was used as an activator of fluorescence and also the polymer constituting the membrane structure, produced a fluorescent coating that was responsive to changes in $CO_2$.

Example 20

Using the formula described in Example 14, the activated fluorescent polymer solution was applied by dropping onto glass coverslips treated with Glass Clad silanizing reagent. The sensors were air dried over night, and remained highly fluorescent after evaporation of the solvent. In gas testing (455 nm excitation, 510 nm emission), the sensor displayed a loss of fluorescence with introduction of $CO_2$: air(0.03% $CO_2$), $I_1$=620; 3% $CO_2$, $I_1$=550; and for 7% $CO_2$, $I_1$=525.

Example 21

Using the formula described in Example 15, the activated fluorescent polymer solution was applied to the glass coverslips treated with Glass Clad silanizing reagent. The sensors were air dried overnight in ambient conditions. With gas testing of the fluorescence dependency on $CO_2$ concentration, the sensor displayed a loss of fluorescence with introduction of $CO_2$: air, $I_1=290$, and 7% $CO_2$, $I_1=250$.

Example 22

Preparation of $O_2$ sensor with quaternary ammonium ion activated fluorescence

One can prepare sensors for other analytes by immobilization of an activated fluorophore that is modulated by a particular analyte. Oxygen has been known to quench the fluorescence of immobilized pyrene derivatives and some work was directed towards preparation of an oxygen sensor with an activated fluorophore in a low dielectric media. The sensor showed a small response to oxygen which may have improved upon optimization of the preparation.

A 5% polystyrene solution was prepared with toluene. To 2 ml polymer was added 0.2 ml pyrenetetrasulphonate ($10^{-3}$ M, abs. ethanol) and 0.06 ml tetrabutylammonium hydroxide. (1.0 M, methanol). The polymer/dye solution was spincoated onto cover slips and the solvent evaporated over night. The sensor was tested for fluorescence quenching (375 nm excitation, 404 nm emission) due to $O_2$: 100% $O_2$, $I_1=529$, 0% $O_2$, $I_1=565$.

Alternate Embodiments

The discussion has addressed the application of this chemistry for fluorescence activation in a solution as well as in a solid media, and the use of the latter as an optical sensor.

Other applications may be realized, particularly in organic chemistry. The addition of an AcOC to a low dielectric media used for extraction of a fluorophore in a separations step may enhance the ability to detect the desired fluorophore. Another variation would be the inclusion of an AcOC in a chromatography scheme to aid isolation of a fluorescent product from a low dielectric solvent system.

After having learned of the above novel development, further variations will be apparent to those with skill in the art.

TABLE 1

Comparative fluorescence activation of HPTS by four quaternary ammonium compounds.
$I_0$, Activated HPTS (5E-7M) with 0.05 mM AcOC

| | AcOC = | | | |
|---|---|---|---|---|
| SOLVENT | Tetra-butyl N+OH– | Tetra-methyl N+OH– | Benzyl-trimethyl N+OH– | Benzyl-trimethyl N+MeO– |
| Hexane | 480 | 20 | 50 | 60 |
| Toluene | 450 | 80 | 220 | 180 |
| 2-Butanol | 230 | 190 | 300 | 360 |
| Methanol | 130 | 400 | 325 | 225 |

TABLE 2

Comparative fluorescence of fluorophores in polymer media, w and w/o quaternary ammonium activation reagent (AcOC).

| | | | | | FLUORESCENCE | |
|---|---|---|---|---|---|---|
| Dye | Polymer | Excitation Wavelength | Emission Wavelength | AcOC/Dye Molar Ratio | Control | Activated Fluorophore |
| 1 Fluorescein | Polystyrene | 485 nm | 518 nm | 0 | 7 | |
| 2 " | " | " | " | 300 | | 326 |
| 3 8-Hydroxy-1,3,6-pyrenetrisulfonic acid Trisodium Salt (HPTS) | Polystyrene | 465 nm | 510 nm | 0 | 16 | |
| 4 8-Hydroxy-1,3,6-pyrenetrisulfonic acid Trisodium Salt (HPTS) | " | " | " | 345 | | 1265 |
| 5 1,3,6,8-Pyrenetetra-sulfonic Acid Tetrasodium Salt | Polystyrene | 375 nm | 404 nm | 0 | 30 | |
| 6 1,3,6,8-Pyrenetetra-sulfonic Acid Tetrasodium Salt | " | " | " | 300 | | 925 |

TABLE 3

Comparative fluorescence activation of fluorescein in four solvents, after addition of tetrabutylammonium hydroxide (TBAH).

| Fluorescein (5E-7M) Solvent | $I_0$, no TBAH | $I_1$, with TBAH | $I_1 - I_0$ | TBAH, mM |
|---|---|---|---|---|
| Hexane | 8 | 394 | 386 | 0.48 |
| Toluene | 9 | 279 | 270 | 0.71 |
| Tetrahydrofuran | 10 | 280 | 270 | 1.32 |
| 2-Butanol | 250 | 300 | 50 | 0.05 |

What is claimed is:

1. A method for measuring an analyte which changes the fluorescence of a fluorophore, wherein said analyte can permeate through a low dielectric medium, comprising
   a. incorporating a fluorophore and quaternary onium compound in a low dielectric medium, said fluorophore being a polyanionic fluorescent dye which undergoes a complete loss of fluorescence when solublized in a low dielectric medium, said fluorescence being restored by the presence of the quaternary onium compound,
   b. measuring the fluorescence,
   c. exposing said medium to a solution containing the analyte to be measured, d. measuring the fluorescence change due to the analyte, and e. determining the concentration of the analyte by reference to a calibration curve.

2. A method of claim 1 in which such analyte is capable of penetrating the low dielectric medium and interacting with the activated fluorophore in a manner that causes a loss in fluorescence.

3. A method of claim 1 in which the analyte is selected from the group consisting of carbon dioxide, oxygen, ammonia and a gaseous byproduct of an enzyme reaction.

4. A method of claim 1 in which a. the fluorophore is selected from the group consisting of fluorescein and derivatives, sulphonated pyrenes and derivatives, seminaphthorhodafluors and derivatives, and seminaphthofluoresceins and derivatives, and b. the analyte is selected from the group consisting of carbon dioxide, oxygen, anunonia, and a gaseous byproduct of an enzyme reaction.

5. A method of claim 1 in which such analyte is capable of penetrating the low dielectric medium and interacting with the activated fluorophore in a manner that increases the fluorescence.

6. A method of claim 3 in which the analyte is carbon dioxide or oxygen.

7. A method of claim 3 in which the analyte is ammonia.

8. A method of claim 3 in which the analyte is a gaseous byproduct of an enzyme reaction.

9. An optical sensing device for determining the concentration of an analyte comprising a polyanionic fluorophore and quaternary onium compound in a low dielectric polymer membrane on the surface of an optical component which is transparent to incident and emissive electromagnetic waves, optically connected to means for collecting the radiant emission to measure the fluorescence indicative of the concentration of the analyte.

10. A device of claim 9 where the fluorophore and quaternary onium compound are included in the low dielectric media optical component.

11. A device of claim 9 wherein the device is an optical fiber.

12. A device of claim 9 wherein the device is a planar waveguide.

13. A device of claim 9 wherein the device is an evanescent wave sensor.

14. A device of claim 9 which contains two or more sensors.

* * * * *